United States Patent [19]

Baglin et al.

[11] 4,181,630

[45] Jan. 1, 1980

[54] CATALYST FOR SYNTHESIS OF METHANOL

[75] Inventors: Elizabeth G. Baglin; Gary B. Atkinson, both of Reno; Larry J. Nicks, Fernley, all of Nev.

[73] Assignee: The United States of America as represented by the Secretary of the Interior, Washington, D.C.

[21] Appl. No.: 964,860

[22] Filed: Nov. 30, 1978

[51] Int. Cl.$^2$ .................. B01J 23/10; B01J 23/12; B01J 23/72
[52] U.S. Cl. .................. 252/476; 252/462; 252/463; 260/449.5; 252/373
[58] Field of Search ............ 252/462, 463, 476, 373; 260/449.5

[56] References Cited

U.S. PATENT DOCUMENTS

| 1,917,323 | 7/1933 | Pier et al. | 260/449.5 |
| 3,790,505 | 2/1974 | Casey et al. | 252/476 X |

FOREIGN PATENT DOCUMENTS

| 308181 | 3/1929 | United Kingdom | 252/462 |

*Primary Examiner*—W. J. Shine
*Attorney, Agent, or Firm*—William S. Brown; Donald A. Gardiner

[57] ABSTRACT

A catalyst for synthesis of methanol is prepared from an alloy of copper with a metal from the rare earth or actinide series or group IVB of the periodic table. The alloy is reacted with a gas having sufficient oxidizing power to oxidize the rare earth, actinide or group IVB metal.

8 Claims, No Drawings

CATALYST FOR SYNTHESIS OF METHANOL

This invention relates to synthesis of methanol by reaction of carbon monoxide, and/or carbon dioxide, and hydrogen in the presence of a catalyst at elevated temperature and pressure. Conventional processes for synthesis of methanol include high pressure synthesis, i.e., at pressure of 100–600 atm and temperature of 250–400° C. using, typically, a zinc oxide based catalyst containing a promoter such as $Cr_2O_3$, and low pressure synthesis at 20–100 atm pressure and 230–300° C. temperature using a catalyst composed of CuO and ZnO, usually in conjunction with $Cr_2O_3$ or $Al_2O_3$. The CuO is reduced prior to use, generally with a dilute $H_2$/inert gas mixture. Improved performance of the catalytically active elements in such processes is, however, highly desirable in order to reduce plant size and energy consumption.

It has now been found, according to the process of the invention, that an efficient catalyst for methanol synthesis may be prepared by treatment of an alloy comprising (1) copper and (2) a second metal from the group consisting of yttrium, a metal from the rare earth or actinide series, and a metal from group IVB of the periodic Table, in a gaseous atmosphere in order to oxidize the second metal without substantial oxidation of the copper. The resulting catalyst comprises an intimate mixture of elemental copper and an oxide of the second metal.

The second metal may consist of a single metal of the rare earth or actinide series, i.e., the elements of atomic numbers 57 to 71 and 89 to 92, respectively, or yttrium, or of group IVB, i.e., titanium, zirconium or hafnium, or a mixture of two or more of any of these metals. Preparation of the alloy of copper and the second metal is accomplished by consolidation of the two by conventional means such as arc-melting in an inert atmosphere or prolonged heating in an inert container sealed under vacuum. Proportions of copper and second metal, or mixture of metals, is not critical and the amount of copper may vary from about 5 to 95 weight percent, preferably about 10 to 70 percent of the alloy.

The gaseous atmosphere may comprise gases of relatively high oxidizing power such as air, mixtures of air and water vapor, oxygen, etc. However, since such gases may result in some degree of oxidation of the copper, a subsequent treatment with a reducing gas, or mixture of gases, such as hydrogen, a mixture of hydrogen and carbon monoxide, etc, may be necessary to reduce any oxides of copper substantially to elemental copper, while leaving the second metal in the oxidized form.

Alternatively, the gaseous atmosphere may comprise a gas, or gases, of lower oxidizing power, such as carbon dioxide or mixtures of hydrogen and carbon monoxide, hydrogen and water vapor, etc, capable of oxidizing the second metal without substantial oxidation of the copper.

The alloy is initially crushed or ground, if necessary, to a particle size suitable for use in methanol synthesis. It is then reacted with the oxidizing gas, or gaseous mixture, for a time, and at a temperature and pressure, sufficient to substantially completely oxidize the second metal with minimal oxidation of the copper. Reaction of the alloy with the oxidizing gas may be carried out in any conventional apparatus capable of providing the desired temperature, pressure and gaseous atmosphere.

The gaseous atmosphere is most conveniently provided by means of a flow of the oxidizing gas through the reactor at a suitable space velocity, e.g., about 100 to 1000 $hr^{-1}$. Generally, an elevated reaction temperature, e.g., about 200 to 500° C. will be preferred in order to provide a suitable reaction rate. However, ambient temperature may be sufficient with some combinations of alloys and oxidizing gases.

Ambient pressure is generally satisfactory, although pressures as high as about 100 atm may be employed. Optimum time of the reaction will be that required to substantially completely oxidize the second metal, preferably without oxidation of the copper, and will depend on the specific alloy, composition and flow rate of the gas, and temperature and pressure employed. The time required will generally be in the range of about 10 to 30 hrs.

Methanol synthesis, using the catalyst of the invention, is carried out according to conventional procedures in which a mixture of hydrogen and carbon monoxide and/or carbon dioxide, in a ratio of approximately 2:1, are reacted at a temperature of about 150 to 360° C. and a pressure of about 20 to 100 atm, with a space velocity of the reactant gas mixture of about 10,000 to 100,00 $hr^{-1}$. Optimum reaction conditions will depend on the specific catalyst employed and are best determined experimentally.

Since the reaction conditions employed in the methanol synthesis reaction may be essentially the same as those used in preparation of the catalyst, where certain alloy compositions are employed, catalyst preparation and methanol synthesis may, in such instances, be a continuous process in which the catalyst if formed initially, with subsequent catalysis of the $H_2$-CO reaction to form methanol.

Preparation of the catalyst and its uses in methanol synthesis will be more specifically illustrated by the following examples.

While these examples describe use of the catalyst in its pure form, it will be obvious to those skilled in the art of catalyst preparation that the active catalyst could also be combined with various inert carriers or binders such as silica, alumina, clays, etc., and formed by methods such as tabletting pelletizing or extrusion into bodies with specific desirable combinations of size, shape, porosity, and mechanical strength.

EXAMPLE 1

An alloy containing 42.2 wt-pct thorium and 57.8 wt-pct copper was prepared by arc-melting the components on a water-cooled copper hearth in a helium atmosphere. The alloy was ground to −25/+80 mesh and 3.00 grams were oxidized in flowing air at 400° C. for 22 hours. X-ray diffraction showed the presence of $ThO_2$, $Cu_2O$, CuO and Cu metal. Surface area measured by a standard gravimetric BET nitrogen adsorption method was 11.1 $m^2/g$. A sample weighing 0.67 grams (0.2 cc) was loaded into a ¼-inch inside diameter stainless-steel tube reactor. Helium was used to pressurize and flush the reactor. After out-gassing, the helium was replaced with a gas mixture analyzing 93.82 pct $H_2$-6.18 pct CO at 60 atm pressure and a standard space velocity of 30,900 $hr^{-1}$. Methanol synthesis activity data were recorded at temperatures between 220° C. and 320° C. Maximum activity was attained at 290° C. with the product (excluding $H_2$) containing 27 mole pct methanol. After the methanol synthesis tests, X-ray diffraction indicated $ThO_2$ and Cu. The BET surface area had increased to 26.0 $m^2/g$.

EXAMPLE 2

An alloy containing 35.39 wt-pct copper and 64.61 wt-pct thorium was prepared by arc-melting the components on a water-cooled copper hearth in a helium atmosphere. After standing three days in air at ambient temperature and pressure, the alloy button had disintegrated into fine granules. X-ray analysis indicated the presence of $ThO_2$, Cu, $Cu_2O$, and CuO. Surface area, measured by the BET method, was 9.4 $m^2/g$ for the $-25/+80$ mesh portion. A sample weighing 0.57 gram (0.2 cc) was loaded into a ¼-inch inside diameter stainless-steel tube reactor. Helium was used to pressurize and flush the system. After outgassing, the helium was replaced with a gas mixture analyzing 94.23 pct $H_2$-5.77 pct CO at 60 atm pressure and a standard space velocity of 29,600 $hr^{-1}$. Methanol synthesis activity data were recorded at temperatures between 240° C. and 300° C. Maximum activity was attained at 270° C. with the product (excluding $H_2$) containing 40 mole pct methanol. After the methanol synthesis test, X-ray diffraction indicated $ThO_2$ and Cu. The BET surface area measured 38.2 $m^2/g$.

EXAMPLE 3

An alloy containing 52.44 wt-pct cerium and 47.56 wt-pct copper was prepared by heating the components to 900° C. for approximately 3 hours in an evacuated quartz tube and then at 800° C. for 19 hours. The alloy was ground to $-25/+80$ mesh. A 2.00 gram sample was treated with $H_2$-$H_2O$ at 400° C. for 24 hours. X-ray diffraction showed the presence of $CeO_2$ and Cu. The BET surface area was 9.5 $m^2/g$. A 0.70 gram sample (0.2 cc) was loaded into a ¼-inch inside diameter stainless-steel tube reactor. Helium was used to pressurize and flush the reactor. After outgassing, the helium was replaced with a gas mixture analyzing 93.85 pct $H_2$-6.15 pct CO at 60 atm pressure and a standard space velocity of 31,500 $hr^{-1}$. Methanol synthesis activity was tested from 220° C. to 360° C. Maximum activity was obtained at 340° C. yielding a product mixture containing 7.0 mole-pct methanol (excluding $H_2$). After the methanol synthesis tests, X-ray diffraction showed the presence of $CeO_2$ and Cu. The BET surface area was 9.9 $m^2/g$.

EXAMPLE 4

An alloy containing 35.97 wt-pct hafnium and 64.03 wt-pct copper was prepared by arc-melting the components on a water-cooled copper hearth in a helium atmosphere. The alloy was ground to $-16/+80$ mesh and 4.0 grams were treated in synthesis gas ($3H_2$-CO) at 10 atm pressure and 400° C. for 23 hours. X-ray diffraction showed elemental copper and a primarily noncrystalline phase which appeared to be $HfO_2$. The BET surface area was 29.4 $m^2g$. A sample weighing 0.67 grams (0.22 cc) was loaded into a ¼-inch inside diameter stainless-steel tube reactor. Helium was used to pressurize and flush the reactor. After outgassing, the helium was replaced with a gas mixture analyzing 93.85 pct $H_2$-6.15 pct CO at 60 atm pressure and a standard space velocity of 32,700 $hr^{-1}$. Methanol synthesis activity was evaluated from 240° to 340° C. Maximum activity was attained at 320° C., yielding a product (excluding $H_2$) containing 9.6 mole pct methanol. After the methanol synthesis tests, the X-ray diffraction pattern had not changed. The BET surface area was 29.8 $m^2/g$.

We claim:
1. A method for preparation of a catalyst comprising:
   a. forming an alloy of copper and a second metal or combination of metals from the group consisting of yttrium, rare earth metals, actinide metals and metals of group IVB of the periodic table; and
   b. reacting said alloy in a gaseous atmosphere in order to oxidize the second metal without substantial oxidation of the copper.
2. The method of claim 1 in which the second metal consists essentially of thorium.
3. The method of claim 1 in which the alloy is initially reacted in an atmosphere consisting essentially of air, and subsequently in an atmosphere consisting essentially of a mixture of hydrogen and carbon monoxide.
4. The method of claim 3 in which the reaction in air is conducted at a temperature of about 200 to 500° C. for a period of about 10 to 30 hours.
5. The method of claim 1 in which the alloy is reacted in an atmosphere comprising a mixture of hydrogen and water vapor.
6. The method of claim 1 in which the alloy is reacted in an atmosphere comprising a mixture of hydrogen and carbon monoxide.
7. The method of claim 1 in which the alloy is reacted in an atmosphere of carbon dioxide.
8. A catalyst prepared by the method of claim 1.

* * * * *